(12) United States Patent
Crabtree et al.

(10) Patent No.: US 9,035,080 B2
(45) Date of Patent: May 19, 2015

(54) PROCESS FOR RECOVERING HOMOGENEOUS METAL HYDRIDE CATALYSTS

(75) Inventors: Simon Peter Crabtree, Durham (GB); Robert Wild, Stockton-on-Tees (GB); Simon Wayne Jackson, Durham (GB); James Andrew Banister, Durham (GB)

(73) Assignee: Davy Process Technology Limited, London (GB)

( * ) Notice: Subject to any disclaimer, the term of this patent is extended or adjusted under 35 U.S.C. 154(b) by 0 days.

(21) Appl. No.: 13/295,855

(22) Filed: Nov. 14, 2011

(65) Prior Publication Data

US 2012/0130102 A1 May 24, 2012

Related U.S. Application Data

(63) Continuation of application No. 10/479,070, filed as application No. PCT/GB02/02577 on May 29, 2002, now abandoned.

(30) Foreign Application Priority Data

May 30, 2001 (GB) .................................. 0113079.8

(51) Int. Cl.
| | | |
|---|---|---|
| *C07F 19/00* | (2006.01) | |
| *B01J 31/12* | (2006.01) | |
| *B01J 31/20* | (2006.01) | |
| *B01J 31/24* | (2006.01) | |
| *B01J 31/40* | (2006.01) | |
| *B01J 38/74* | (2006.01) | |

(Continued)

(52) U.S. Cl.
CPC ............... *B01J 31/121* (2013.01); *B01J 21/08* (2013.01); *B01J 31/08* (2013.01); *B01J 31/20* (2013.01); *B01J 31/2404* (2013.01); *B01J 31/4038* (2013.01); *B01J 31/4046* (2013.01); *B01J 31/4069* (2013.01); *B01J 31/4092* (2013.01); *B01J 38/74* (2013.01); *B01J 2231/321* (2013.01); *B01J 2531/82* (2013.01); *B01J 2531/822* (2013.01); *C07C 45/50* (2013.01)

(58) Field of Classification Search
None
See application file for complete search history.

(56) References Cited

U.S. PATENT DOCUMENTS

| 3,755,393 A | 8/1973 | Kniese et al. |
|---|---|---|
| 4,021,463 A | 5/1977 | Kummer et al. |

(Continued)

FOREIGN PATENT DOCUMENTS

| WO | WO 97/03938 | 2/1997 |
|---|---|---|
| WO | WO 00/09520 | 2/2000 |

OTHER PUBLICATIONS

Katayama et al. Journal of Chemical and Engineering Data, vol. 21, No. 2, 1976, 194-196.*

*Primary Examiner* — Yun Qian
(74) *Attorney, Agent, or Firm* — Davidson, Davidson & Kappel LLC

(57) ABSTRACT

The present invention relates to a process for recovery of homogeneous metal hydride catalyst from a reactor stream as catalyst suitable for recycle to a reactor comprising the steps of: removing a stream from a reactor, said stream comprising the homogeneous metal hydride catalyst; contacting the stream with a solid acidic absorbent under process conditions which allow at least some of the metal to become bound to the absorbent; subjecting the metal bound to the absorbent, under process conditions which allow desorption of the metal, to a fluid stripping medium comprising hydrogen and solvent; and recovering the active metal hydride catalyst.

19 Claims, 1 Drawing Sheet

(51) Int. Cl.
 *C07C 45/50* (2006.01)
 *B01J 21/08* (2006.01)
 *B01J 31/08* (2006.01)

(56) References Cited

U.S. PATENT DOCUMENTS

| | | | |
|---|---|---|---|
| 4,113,754 A | 9/1978 | Kummer et al. | |
| 4,203,952 A | 5/1980 | Hancock et al. | |
| 4,221,743 A | 9/1980 | Halstead et al. | |
| 4,297,239 A | 10/1981 | Bryant et al. | |
| 4,388,279 A | 6/1983 | Quick | |
| 4,390,473 A | 6/1983 | Cooper | |
| 4,482,749 A | 11/1984 | Dennis et al. | |
| 4,929,767 A | 5/1990 | Miller et al. | |
| 4,985,540 A | 1/1991 | Bradford et al. | |
| 5,085,835 A | 2/1992 | Weber et al. | |
| 5,091,546 A | 2/1992 | Lappe et al. | |
| 5,151,537 A | 9/1992 | Lappe et al. | |
| 5,208,194 A | 5/1993 | Pitchai et al. | |
| 5,237,106 A * | 8/1993 | Babin et al. | 568/454 |
| 5,264,600 A | 11/1993 | Lappe et al. | |
| 5,294,415 A | 3/1994 | Lappe et al. | |
| 5,773,665 A | 6/1998 | Silverman et al. | |
| 5,936,130 A | 8/1999 | Mori et al. | |
| 6,946,580 B2 | 9/2005 | Banister et al. | |

* cited by examiner

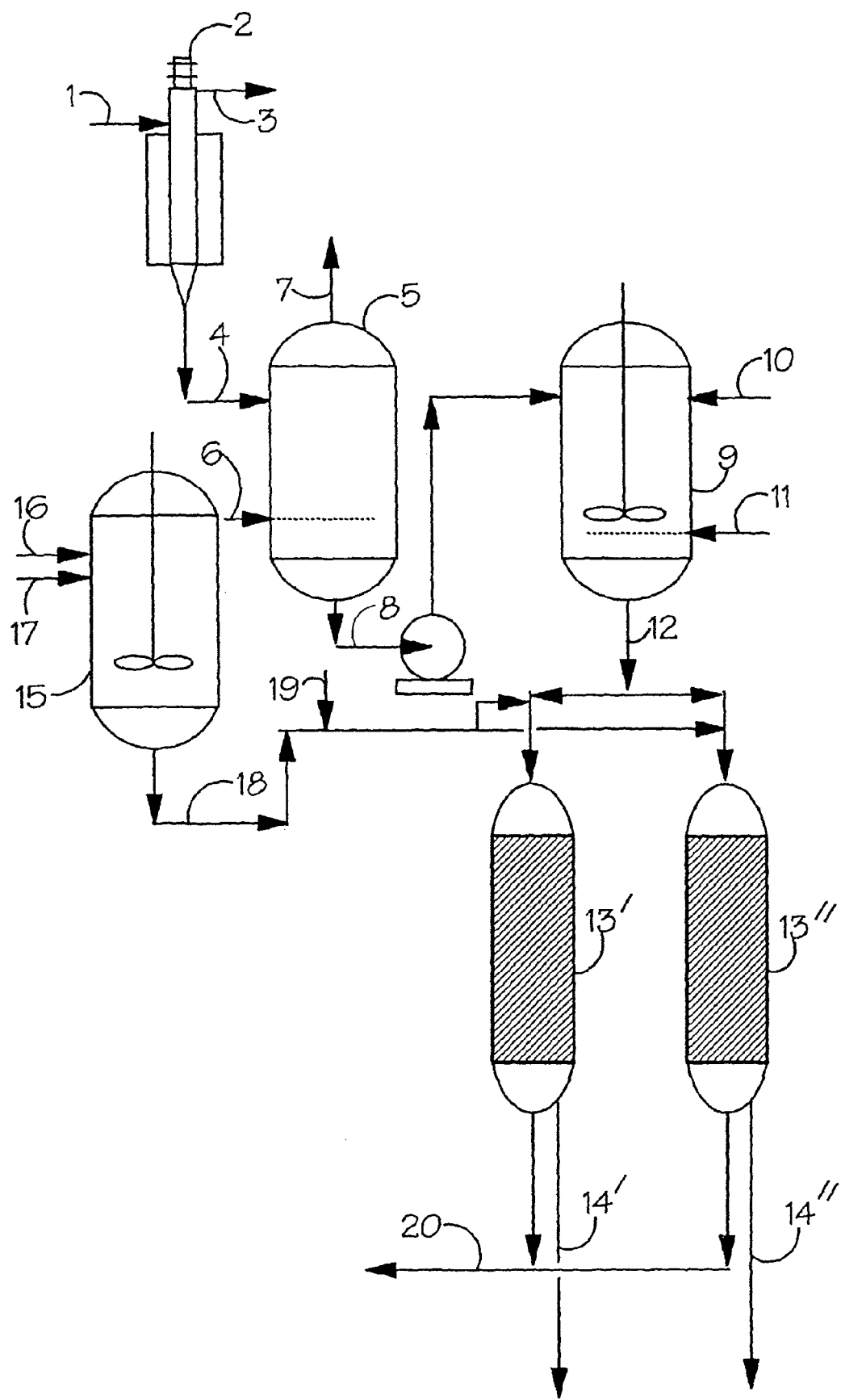

US 9,035,080 B2

PROCESS FOR RECOVERING HOMOGENEOUS METAL HYDRIDE CATALYSTS

This application is a continuation of U.S. patent application Ser. No. 10/479,070, filed Apr. 19, 2004, now abandoned which is a national phase application under 35 U.S.C. §371 of International Application No. PCT/GB02/02577 filed May 29, 2002 which claims priority to Great Britain Application No. 0113079.8 filed May 30, 2001, the disclosures of which are all hereby incorporated by reference herein.

BACKGROUND OF THE INVENTION

The present invention relates to a process for recovering transition metal catalysts. More particularly it relates to a process for recovering Group VIII noble metal catalysts in active form. Most particularly it relates to a process for recovering rhodium catalysts in active form.

Group VIII noble metal complexes are commonly used as homogeneous catalysts in a variety of organic reactions. Of these catalysts, the rhodium complexes are particularly useful in hydroformylation reactions in which an olefin is reacted with hydrogen and carbon monoxide in the presence of the catalyst to yield an aldehyde. Complexes of rhodium with organophosphorous ligands such as triphenylphosphine and triphenylphosphite are particularly attractive catalysts as they favour the formation of the desired aldehyde products. In some cases the selectivity for the desired aldehyde may be in the region of 90% or more when the appropriate phosphorous ligand is present.

However, whilst these catalysts are very effective, they suffer from a major drawback associated with their cost. It is therefore desirable to recover these highly expensive metals from the organic solutions in which they are removed from the reactor. Further, during operation, the catalyst may become deactivated and therefore needs to be removed from the reactor such that fresh active catalyst can be added. The removed catalyst will generally be reprocessed to recover the metal values.

The deactivated catalyst may have been thermally deactivated i.e. clustered and/or chemically deactivated i.e. poisoned or inhibited.

In some cases although the catalyst may be chemically active, the catalyst solution includes such a high concentration of non-volatile material that it is of no further practical use.

Although the mechanism of deactivation in aryl phosphine liganded systems by the formation of clusters is not entirely clear, it is believed that metal, e.g. rhodium clusters, having phosphido bridges may be formed, for example, by the loss of one or more phenyl groups from the aryl phosphine molecule. The chemical deactivation may be poisoning such as sulphur compounds, chloride, cyanide and the like.

The chemical deactivation may also be inhibition of the catalyst. Inhibitors that may be found in, for example, propylene and butylene hydroformylation include acetylenes and acroleins.

Conventionally, the operators of the plant have had to collect the active and/or inactive catalyst by shutting down the reactor, removing the catalyst in solution and concentrating it to partially separate it from the other components present. Additionally, or alternatively, catalyst may be collected from one or more reactor streams. By reactor stream we mean any stream which is obtained from any point in a process and which will contain Group VIII noble metal catalyst.

The Group VIII noble metals have conventionally been removed from the organic solutions by a variety of means before being shipped off-site for regeneration. This means that if the operation of the plant is not to be shut down for a prolonged period, the operator must purchase more of the very expensive catalyst to operate the plant than he actually requires at any one time.

There are also environmental issues associated with the regeneration of the catalyst where phosphorous ligands are present.

A variety of means of recovering the Group VIII noble metals from solution has been suggested including precipitation followed by extraction or filtration and extraction from the organic mixtures using, for example, amine solutions, acetic acid, or organophosphines. The organic solution of a deactivated solubilized catalyst may be treated to improve the extractability of the metal. Examples of this may be found in U.S. Pat. No. 4,929,767 and U.S. Pat. No. 5,237,106 which are incorporated herein by reference.

Ion-exchange methods have also been suggested, for example in U.S. Pat. No. 3,755,393 which describes passing a hydroformylation mixture through a basic ion-exchange resin to recover rhodium. A similar process is described in U.S. Pat. No. 4,388,279 in which Group VIII metals are recovered from organic solution using either a solid absorbent such as calcium sulfate, an anionic ion-exchange resin or molecular sieves.

An alternative arrangement is described in U.S. Pat. No. 5,208,194 in which a process is described for removing Group VIII metals from organic solutions which comprises contacting the organic solution with an acidic ion-exchange resin containing sulfonic acid groups. The treated solution is then separated from the ion-exchange resin and the metal values are recovered from the resin by any suitable means. The means that is suggested is that the resin should be burnt off in an ashing process which leaves the metal in a form suitable for recovery.

These prior art processes, whilst being suitable for separating the metal from the stream in which it was removed from the reaction, suffer from the disadvantage that the operator of the reactor must send the recovered metal concentrate off site to be converted into an active form. Further, where the stream removed from the reactor includes active catalyst, the separation procedure will either leave it in a form in which it cannot be returned to the reactor or will cause it to be deactivated such that it is no longer suitable for use in the reactor and removal off-site for regeneration is required.

In U.S. Pat. No. 5,773,665, a process is suggested which enables active catalyst contained in a stream removed from a hydroformylation process to be separated from the inactive catalyst and the active catalyst following treatment, to be returned to the hydroformylation reactor. In the process a portion of the recycle stream from the hydroformylation reaction is passed through an ion exchange resin column to remove impurities and active rhodium and the thus purified recycled stream, which may contain inactive catalyst, is returned to the hydroformylation reactor.

The impurities, which may include aryl phosphine oxide, alkyl phosphine oxide, mixed phosphine oxide and high molecular weight organic compounds, are removed from the resin by washing with, for example, an organic solvent. The effluent from this wash is removed as a waste stream. The active catalyst remains bound to the resin during this washing process.

The resin is then treated with a catalyst removal solvent such as isopropanol/HCl to produce a stream containing "active" rhodium catalyst for eventual recycling to the hydroformylation reactor. Whilst the catalyst has not been deactivated by thermal or chemical means and is therefore referred to as "active" it is not in a form in which it will actually act as a catalyst in the reactor. Thus, before the catalyst can be recycled it must first be removed from the resin using a strong acid reagent and then converted to the hydridocarbonyl by treatment with hydrogen and carbon monoxide in the presence of an acid scavenger and a ligand to make it a truly active catalyst.

In an optional arrangement, the inactive rhodium catalyst, i.e. the clustered catalyst, which passed through the ion-exchange resin without being absorbed and which is contained in the purified recycle stream may be reactivated by conventional technology such as by wiped film evaporation followed by oxidation and subsequent reduction before being returned to the reactor. Thus this inactive catalyst is not treated by the ion-exchange resin.

Whilst this process goes some way to addressing the problems associated with prior art processes, in that it suggests a means of separating the active catalyst on site, it suffers from various disadvantages and drawbacks in particular those disadvantages associated with the need to treat the "active" catalyst after it has been removed from the ion-exchange resin and before it can be returned to the reactor. Indeed it is the ion-exchange treatment which means that the catalyst is no longer suitable for use in the reactor.

Although in a preferred embodiment, U.S. Pat. No. 5,773,665 does suggest that the thermally deactivated catalyst may be regenerated before return to the reactor, the overall plant is expensive to construct and operate because of the number of separation and treatment steps, some of which occur in the presence of corrosive acid media, required to achieve full recycle. A further drawback associated with the presence of acid media is the further complexity and costs associated with the consumption of base required to neutralise the acid and dispose of the acid salts.

There is therefore a desire to produce a process for the recovery of Group VIII noble metal catalysts the plant for which is simple and cost-effective to construct and to operate.

SUMMARY OF THE INVENTION

A process has now been developed which enables the catalytic metal, whether catalytically inactive or active, to be separated from the stream from the reactor by a suitable absorbent, such as an ion-exchange resin, and then removed from the absorbent in a form which is suitable for return to the reactor. Whilst the process is particularly effective at allowing rhodium catalysts from a hydroformylation reactor to be recovered and regenerated for return to the reactor, it is also suitable for regenerating other Group VIII catalysts for use in other reactors.

Thus, according to the present invention there is provided a process for recovery of a homogeneous Group VIII noble metal hydride catalyst from a reactor stream as catalyst suitable for recycle to a reactor comprising the steps of:
(a) removing a stream from a reactor, said stream comprising the homogeneous Group VIII noble metal hydride catalyst;
(b) contacting the stream with a solid acidic absorbent under process conditions which allow at least some of the metal to become bound to the absorbent;
(c) subjecting the metal bound to the absorbent, under process conditions which allow desorption of the metal, to a fluid stripping medium comprising hydrogen and a solvent; and
(d) recovering the active Group VIII noble metal hydride catalyst.

Thus the metal hydride catalyst removed from the acidic absorbent is recovered in an active state and can be recycled to the reactor.

The fluid stripping medium may comprise hydrogen and a process compatible solvent in a single fluid phase, which may be a supercritical phase. In one alternative arrangement the fluid stripping medium comprises hydrogen and a process compatible solvent in a two phase system. In one arrangement, the process compatible solvent may be a solvent or reactant of the reaction.

Where the fluid stripping medium comprises a liquid phase and a gas phase, the ratio of the gas phase to the liquid phase may be any suitable value. One suitable example would be one volume of gas to ten volumes of liquid.

Where the fluid is a single phase, the ratio of dissolved hydrogen to solvent present may be any suitable value and may be similar to that used for the two phase system. An important parameter is that an appropriate amount of hydrogen is present.

In one arrangement, the solvent is a liquid which is contacted with a gas phase including hydrogen until it is partially or totally saturated with dissolved gases. The liquid may then be separated from the gas phase prior to being passed over the metal containing absorbent as a single phase. The saturated solution may be increased in pressure before being passed over the absorbent as the stripping medium.

Supercritical propane or carbon dioxide may be used as process compatible solvent. In this arrangement, a supercritical mixture including hydrogen, an optional co-solvent, and ligand may be used as the stripping fluid.

The metal hydride catalyst is preferably a platinum, palladium, iridium or rhodium hydride catalyst. Most preferably it is a rhodium hydride catalyst such as, for example HRh(CO)(PPh3)3, further details of which can be found in, for example, page 792 of "Advanced Inorganic Chemistry" (Third Edition) by F. Albert Cotton and Geoffrey Wilkinson, published by Interscience Publishers. The process is also suitable for use with other rhodium catalysts, for example those described in U.S. Pat. No. 4,482,749 which is incorporated herein by reference.

The reactor stream may be any stream which is obtained from any point in a process and which will contain metal hydride catalyst in solution. Thus in some reaction schemes, catalyst may be removed from the reactor in product stream or in other streams including purge streams. These streams may be treated in accordance with the present invention to recover this valuable catalyst in a form which is suitable for return to the reactor. The reactor stream may be passed directly for treatment in accordance with the process of the present invention or may first undergo any suitable pretreatment. Where the reactor stream is a product stream, the reaction product may be present during the recovery process of the present invention or may be removed before the stream is contacted with the absorbent.

The present invention is particularly suitable for removing the metal catalyst from reactor streams containing molecules having a high molecular weight and hence low volatility and which are therefore difficult to separate from the catalyst by conventional means.

The various streams from the reactor, following suitable pre-treatment, such as to remove product may be combined for treatment through a single catalyst recovery plant. Alternatively, each stream may be treated separately or streams with similar compositions may be treated together.

The invention is particularly suitable for use with streams removed from a hydroformylation reactor, and most particularly those streams which comprise catalyst and high molecular weight organic compounds known as "heavies", (i.e. high boiling byproducts). Examples of these heavies include organic condensation products and will include cyclic trimers and higher cyclic moieties and linear and branched polymeric moieties which could also be present in the feed to the reactor. These compositions typically have low volatility and can be difficult to separate from the catalyst by conventional techniques.

Thus, the present invention will enable the metal catalyst to be separated from essentially non-volatile components of the stream which can then be removed, with optionally subsequent treatment in accordance with conventional means.

In a preferred arrangement of the present invention the acidic absorbent is an acidic ion exchange resin. The resin may be a styrene divinylbenzene copolymer containing sulphonic acid groups or carboxylic acid groups. The resin may have a siloxane-containing backbone and an acidic functional group attached to the backbone. The acidic functional group is preferably selected from the group consisting of aromatic carboxylic acids, aliphatic carboxylic acids, aromatic sulphonic acids and aliphatic sulphonic acids, with the sulphonic acids being particularly preferred.

Preferably the resin is used in the protonated form. Thus where the sulphonic acid groups are the active groups, they are in the form —SO3H and in the presence of phosphines they are at least partially in the form —SO3(-)[HPR3](+). Neutralized sulphonic acid resins, in which some or all of the protons have been exchanged by a cation may also be suitable but are not preferred.

Particularly preferred resins include Amberlyst™ 15 and Amberlyst™ DPT-1, with Amberlyst™ DPT-1 being most preferred. Amberlyst™ 15 is available from Rohm and Haas (U.K.) Limited of Lennig House, 2 Mason's Avenue, Croydon CR9 3NB, England and Amberlyst™ DPT-1 ion exchange resin is available from Kvaerner Process Technology Limited of The Technology Centre, Princeton Drive, Thornaby, Stockton-on-Tees TS 17 6PY, England.

The absorbent may be pre-treated prior to use. The absorbent may be washed, for example, with methanol to remove water and may also be sieved prior to being contacted with the reactor stream.

Without wishing to be bound by any theory, it is believed that the ion-exchange resin or other suitable absorbent will allow the absorption of the metal hydride species onto its surface by a protonation and subsequent elimination of hydrogen by the reaction of Scheme 1. This hydrogen elimination is a reversible reaction and thus the metal species remains as a labile species and can be desorbed by the hydrogen in the fluid stripping medium.

Scheme 1

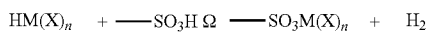

where M is a Group VIII metal, each X is a liganding group which may be the same or different and n is an integer of from 2 to 5.

The contact of the reactor stream with the solid acid absorbed resin may be carried out at any suitable temperature. Temperatures of from 0° C. to about 120° C. may be used with those of from about 20° C. to about 100° C. being preferred. A temperature in the region of from about 65° C. to about 95° C. is particularly preferred as the higher temperature will facilitate the removal of the metal from solution and its loading onto the absorbent. The temperatures and pressures will generally be selected such that any solids formation such as crystallisation of ligand or ligand oxide is avoided.

As the catalyst is absorbed onto the resin, a catalyst depleted solution will remain and may be removed from the system. The further treatment of this solution will depend on the content of the stream. Where the reaction stream treated in accordance with the present invention is a stream containing the heavies from a hydroformylation reaction, the catalyst depleted solution will preferably be removed. The catalyst depleted solution may be passed through a conventional catalyst collection system to trap the inactive catalytic metal and any trace amounts of the catalyst remaining.

The stream to be treated may be concentrated before being contacted with the acidic absorbent. The concentration will preferably occur by removal of volatilisable material. The reactor stream or the concentrated stream may require dilution with a solvent compatible with the absorbent before it is contacted with the absorbent. Any suitable solvent may be used. Normally, the solvent will be miscible with the reactor stream or concentrated stream. Suitable solvents include xylene and toluene.

Where the stream to be treated includes inactive catalyst this may be exposed to the absorbent but may not react therewith and if no reaction occurs will be removed with the non-volatile components.

However, where the inactive catalyst has been deactivated by the formation of clusters, these may be broken before the stream is contacted with the absorbent such that they can be absorbed by the absorbent and treated with the stripping medium. By this means this inactive catalyst may be regenerated such that it may be returned to the reactor and take part in the reaction.

Thus according to a preferred aspect of the present invention, the stream is preferably passed through an oxidiser where air is passed through the solution to break down the clusters before being brought into contact with the absorbent. For a rhodium catalyst having triphenylphosphine as a ligand, the air will break down the rhodium clusters by oxidation of the phosphido bridges.

The oxidiser may also at least partially oxidise any trivalent phosphorous compounds which may be present to the pentavalent form (i.e. conversion from phosphites to phosphates).

Where the oxidiser is present, the oxidation step, in addition to breaking up the clusters, may additionally change the oxidation state of the metal in that it will be converted to a simple cationic form. Thus where the metal is rhodium, Rh2+ and Rh3+ will be formed.

Additionally or alternatively, the reaction stream may be treated in accordance with one or more of the organic reagents described in U.S. Pat. No. 4,929,767 and U.S. Pat. No. 5,237,106 which are incorporated herein by reference.

To improve the absorbability of the metal onto the absorbent, the process may additionally include, treating the catalyst such that it is in a suitable state for absorption.

Where the catalyst is rhodium for use in hydroformylation, the catalyst preferably is subjected to hydrocarbonylation where it is treated with an organophosphorous ligand such as triphenylphosphine, carbon monoxide and hydrogen to reform the catalyst in the form HRh(CO)(PPh3)3.

Once the metal has been loaded onto the absorbent, the absorbent may be washed to further remove impurities. In addition to removing impurities by means of their not being absorbed by the absorbent such that they are removed in catalyst depleted reactor stream or by the washing described above, the absorbent may also serve to remove some impurities. For example, where the catalyst of the reaction is a Group VIII noble metal catalyst, iron, nickel and/or chromium may additionally be present. These will generally also be absorbed by the absorbent but will not be retrieved by the stripping medium of the present invention. Thus the stream recycled to the reactor will be free of these impurities.

Whatever pre-treatments of the stream are carried out, and whatever washing is carried out, if any, the partial pressure of the gaseous phase of the stripping media, or of the hydrogen component of the supercritical phase or the fluid phase, for removing the absorbed metal may be of any suitable value. Partial pressures of about 200 kPa or higher may be particularly advantageous. The upper limit on the partial pressure will be dictated by the equipment rating.

The stripping media fluid preferably additionally includes carbon monoxide. The presence of carbon monoxide has been found to offer improved results. This is particularly appropriate where the metal catalyst complex includes CO as a ligand.

The fluid of the stripping media preferably includes a liquid phase which comprises liquids which are compatible with the reactants, other compounds and products in the reactor, such that the product stream containing the metal hydride catalyst may be returned to the reactor without further processing. The fluid is preferably also compatible with product recovery operations.

In one embodiment of the present invention, the fluid of the stripping media will comprise liquids which are required to be present in the reactor such as ligands and raw materials. Thus, where the catalyst is $HRh(CO)(PPh3)3$ in one arrangement, the liquid phase will comprise triphenylphosphine. Where the reaction is hydroformylation, the liquid phase may comprise olefin and/or triphenylphosphine. Thus, a preferred process of the present invention allows that no additional substances are fed to the reactor other than those required for or produced in the reaction.

In one alternative embodiment, the fluid includes material that is used in the catalyst recovery process but which is inert to the reaction process, for example, the hydroformylation process. The material is preferably recoverable and recyclable from the reaction process to the metal recovery section of the plant. One example of suitable material is toluene which may be used as a solvent or diluent in the metal recovery process.

Whilst the reactor stream may be contacted with the solid absorbent by any suitable means, the absorbent is preferably a resin bed in a column through which the reactor stream flows. Once the resin bed has been loaded with the metal, the stripping medium is then preferably passed through the resin bed and into the reactor. In one alternative arrangement, the reactor stream may be contacted with the absorbent in a stirred vessel. In this arrangement, the contact will be a repeated batch process.

The stripping process will preferably simultaneously regenerate the absorbent bed for further subsequent absorption of metal from a fresh stream. However, it may be advisable to wash the resin at least periodically to remove any impurities, ligand and the like which may build up over several passes of reactor stream.

The stripping may be carried out at similar temperatures as those used for the loading. However, lower temperatures favour the metal being desorbed and going into solution. Suitable temperatures include from about 20° C. to about 70° C. This is particularly the case where higher partial pressures of hydrogen are used.

To allow for continuous treatment of catalyst from the reactor, the plant may include at least two beds of absorbent operated in parallel. The reactor stream will be passed through a first bed of absorbent such that the metal is substantially removed from the stream. Once the bed has been loaded, the stream will be switched to flow through the second bed. Whilst the second bed is being similarly loaded, the stripping medium will be applied to the first bed such that the metal is desorbed. The procedure will then be reversed such that the first bed is being loaded while the second bed is being desorbed. Thus in a preferred arrangement, the process is effectively continuous.

Thus the present invention provides a process the plant for which is cost-effective to construct and to operate and which enables the catalyst to be recovered from reactor streams and returned to the reactor.

A further advantage of the present invention is that where reactants, ligands and the like are used for the stripping medium and these are passed via the absorbent where stripping occurs, to the reactor, not only are no additional substances, or only inert substances, introduced into the reactor, there are no costs associated with the stripping medium.

The recovery of the catalyst in accordance with the present invention may also enable poisoned and/or inhibited catalyst to be reactivated. Without wishing to be bound by any theory, it is believed that the metal is attracted to the absorbent and the poison/inhibitor is removed in the catalyst depleted stream.

The process of the invention is particularly suitable for use in hydroformylation of optionally substituted C3 to C20 olefinically unsaturated hydrocarbons.

BRIEF DESCRIPTION OF THE DRAWINGS

The present invention will now be described, by way of example with reference to the accompanying drawing in which:

FIG. 1 is a schematic diagram of a process in accordance with the present invention.

DETAILED DESCRIPTION OF THE INVENTION

It will be understood by those skilled in the art that the drawings are diagrammatic and that further items of equipment such as feedstock drums, pumps, vacuum pumps, compressors, gas recycling compressors, temperature sensors, pressure sensors, pressure relief valves, control valves, flow controllers, level controllers, holding tanks, storage tanks and the like may be required in a commercial plant. Provision of such ancillary equipment forms no part of the present invention and is in accordance with conventional chemical engineering practice.

For ease of reference, the process of the present invention will be described with reference to the hydroformylation of an olefin to an aldehyde in the presence of a rhodium hydride complex with carbon monoxide and a triphenylphosphine ligand. However, it will be understood that the process is equally applicable to other reactions as described above.

Hydroformylation will occur in a hydroformylation zone containing a charge of a liquid reaction medium having in solution therein the complex rhodium hydroformylation catalyst comprising rhodium, carbon monoxide and triphenylphosphine. The olefin is supplied to the hydroformylation zone which is maintained at temperature and pressure conditions which are conducive to hydroformylation of the olefin. Carbon monoxide and hydrogen will then be supplied such that reaction occurs. The aldehyde product will be removed from the reaction zone. In addition, the reaction zone will be purged of non-volatile condensation components in a "heavies" removal stream. Either of these streams may be the subject of the rhodium recovery process of the present invention. However, for ease of understanding, the further discussions will be made with regard to the "heavies" removal stream.

This stream 1 will be passed to an evaporator, such as a wiped film evaporator 2 to separate any remaining volatile components. Volatile components of the stream will be removed in line 3 and may be subjected to further treatment including condensation and separation. Triphenylphosphine may also be removed in line 3.

The residue of unvaporized portions which will now be a concentrated reactor stream is passed in line 4 to oxidiser 5 where air is bubbled through the liquid. The air is introduced in line 6 and is purged in line 7. The air will serve to break any cluster rhodium molecules so that this previously inactive rhodium can be absorbed by the ion exchange resin.

The stream including the rhodium leaves the oxidiser in line 8 and is then pumped to a hydrocarbonylation zone 9. In this stirred tank vessel, the catalyst containing stream is mixed with triphenylphosphine added in line 10 and is contacted with hydrogen and carbon monoxide which is added in line 11. The triphenylphosphine added via line 10 may be recycled triphenylphosphine recovered from line 3.

The carbonylated catalyst is then removed in line 12 and is passed into the first absorber column 13' which is packed with ion-exchange resin Amberlyst™ DPT-1. The resin bed will be at a temperature in the region of about 85° C. to aid the rate of absorption of the rhodium by the ion-exchange resin.

As the stream passes through the absorbent bed, the rhodium is absorbed onto the resin and the non-volatile heavies and impurities are removed in stream 14' for optional further processing. Due to the value of the rhodium, the stream may be passed through a conventional rhodium recovery system to collect any catalyst which may pass through the resin bed, which may be inactive catalyst, for off-site regeneration.

Once column 13' has been loaded, the stream from vessel 9 will be directed to column 13" so that the removal of the rhodium can be carried out as a continuous process. When the resin is loaded in column 13", the catalyst depleted stream is removed in stream 14".

The rhodium loaded in column 13' is then stripped from the resin using a stripping medium which is passed through the column. Where the stripping medium contains a mixture of organic liquids, these will be combined in mixer 15. The liquid phase is preferably a combination of process compatible solvents and/or olefin added in line 16 and triphenylphosphine added in line 17.

The olefin may be fresh olefin which will be passed through the resin bed before being added to the reactor. Alternatively, the olefin may be recycled olefin, isomerised olefin and paraffin recovered from streams removed from the hydroformylation reactor.

Similarly, the process compatible solvents may be fresh solvents or recycled solvents recovered from streams removed from the hydroformylation reactor or the downstream product recovery systems.

The triphenylphosphine may be fresh triphenylphosphine or it may be recycled, for example from stream 3 of volatile compounds removed from the wiped film evaporator 2.

This combined liquid phase for the stripping medium is removed from the mixer 15 in line 18 where it is combined with hydrogen and carbon monoxide of the gaseous phase which is added in line 19. The stripping medium will be passed through column 13' which is held at ambient or higher temperature.

The resulting stream, which will contain rhodium, hydrogen, carbon monoxide, triphenylphosphine and olefin and/or process compatible solvents is then returned to the reactor in line 20.

The removal of the rhodium allows resin bed 13' to be used to absorb further rhodium. Resin bed 13" can then be stripped by repeating the process described above. Thus the process can be operated in a continuous manner.

The invention is illustrated further in the following Examples.

Example 1

The ability of the Amberlyst DPT-1 to reversibly remove rhodium from an octene hydroformylation reactor solution was investigated using a solution containing 175 ppm rhodium and 10 wt % triphenylphosphine in a solution containing 28 g octene-1 and 52 g toluene. The octene was first converted to nonanal by hydroformylation at 85° C. and 85 psig with 1:1 hydrogen/carbon monoxide with measurement of the gas uptake. 25 ml dry volume of washed and dried Amberlyst DPT-1 was soaked in a solution containing 10 wt % triphenylphosphine in toluene and then filtered. After the octene hydroformylation was shown to be complete by cessation of discernable gas uptake the solution was cooled and the wet resin added to the autoclave. The mixture was then heated to 85° C. for one hour and the liquid drained from the resin. Analysis showed that the rhodium concentration in solution had fallen to 14 ppm. 50 ml of 10 wt % triphenylphosphine in toluene was added to the resin remaining in the reactor. The solution was purged with 1:1 hydrogen/carbon monoxide at atmospheric pressure, heated to 85° C. and pressurised with hydrogen to 85° C. and pressurised with hydrogen to 1000 psig. The autoclave was then allowed to cool. The triphenylphosphine solution was removed from the resin and found to contain 160 ppm rhodium.

Example 2

The effect of poisons on the recovery of hydroformylation catalyst was investigated using a solution containing 175 ppm rhodium and 10 wt % triphenylphosphine in a solution containing 28 g octene-1, 52 g toluene and 1 ml of ethyl sorbate. The octene was first converted to nonal by hydroformylation at 85° C. and 85 psig with 1:1 hydrogen/carbon monoxide with measurement of the gas uptake. From the rate of gas uptake it was calculated that the rhodium had only 50% the activity that would be expected in the absence of poisons and inhibitors. 25 ml dry volume of washed and dried Amberlyst DPT-1 was soaked in a solution containing 10 wt % triphenylphosphine in toluene and then filtered. After the octene hydroformylation was shown to be complete by cessation of discernable gas uptake the solution was cooled and the wet resin added to the autoclave. The mixture was then heated to 85° C. for one hour and the liquid drained from the resin. Analysis showed that the rhodium concentration in solution had fallen to 25 ppm. 50 ml of 10 wt % triphenylphosphine in a toluene solution containing 14 g octene was added to the resin remaining in the reactor. The solution was purged with 1:1 hydrogen/carbon monoxide at atmospheric pressure, heated to 85° C. and pressurised with hydrogen to 85° C. and pressurised with hydrogen to 1000 psig. The autoclave was then allowed to cool. The triphenylphosphine solution was removed from the resin and found to contain 150 ppm rhodium. This solution was then made up to 100 ml using further octene, toluene and triphenylphosphine, replaced in the cleaned reactor and pressurised with 1:1 hydrogen/carbon monoxide at 85° C. and 85 psig. From the rate of gas uptake it was determined that the activity of the solution was 98% of the activity that would be expected from an uninhibited solution.

Example 3

The effect of hydrogen pressure on the concentration of the hydroformylation catalyst in solution was investigated using 200 ml of a solution containing 570 ppm rhodium and 10 wt % triphenylphosphine in octene-1. First the solution was gradually heated up to 85° C. and 85 psig 1:1 hydrogen/carbon monoxide until hydroformylation was complete. After cooling, 50 ml of washed and dried Amberlyst DPT-1 was added to the reactor and warmed to 95° C. with stirring. After heating at 95° C. for 4 hours the solution was removed and the rhodium concentration was determined to be 18 ppm. 100 ml of 10 wt % triphenylphosphine in toluene was then added to the autoclave and stirred at 40° C. and 500 psig of hydrogen for 16 hours. A sample taken from the reactor after this time contained 330 ppm rhodium. The pressure in the autoclave was then released and the temperature increased to 70° C. After 2 hours a sample was taken and analysed and found to contain 24 ppm rhodium. The pressure in the autoclave was increased again to 500 psig and sampled after 30 minutes after which time the solution contained 150 ppm rhodium.

The invention claimed is:

1. A process for recovery of homogeneous Group VIII noble metal hydride catalyst from a reactor stream as catalyst suitable for recycle to a reactor comprising the steps of:
    (a) removing a stream from a reactor, said stream comprising deactivated homogeneous Group VIII noble metal hydride catalyst;
    (b) contacting the stream with a solid acidic absorbent under process conditions which allow at least some of the metal to become bound to the absorbent;
    (c) subjecting the metal bound to the absorbent to a fluid stripping medium comprising hydrogen and a solvent, under process conditions which allow the metal to be desorbed from the absorbent and rehydrided at a pressure above 200 kPa to form an active Group VIII noble metal hydride catalyst; and
    (d) recovering the homogeneous active Group VIII noble metal hydride catalyst.

2. A process according to claim 1 wherein the fluid stripping medium is a single fluid phase.

3. A process according to claim 1 wherein the fluid stripping medium comprises two fluid phases.

4. A process according claim 1 wherein the Group VIII noble metal hydride catalyst is a platinum, palladium, iridium or rhodium hydride catalyst.

5. A process according to claim 4 wherein the catalyst is $HRh(CO)(PPh_3)_3$.

6. A process according to claim 1 wherein the reactor stream is from a hydroformylation reactor.

7. A process according to claim 6 wherein the reactor stream contains non-volatile by-products of the reaction.

8. A process according to claim 1 wherein the reactor stream having been contacted with the solid acidic absorbent is removed.

9. A process according to claim 1 wherein the acidic absorbent is an ion-exchange resin.

10. A process according to claim 1 wherein the acidic absorbent is a styrene divinyl copolymer containing sulphonic acid groups or carboxylic acid groups.

11. A process according to claim 1 wherein the acidic absorbent has a silica-containing backbone and an acidic functional group attached to the silica.

12. A process according to claim 11 wherein the acidic functional group is an aromatic carboxylic acid, an aliphatic carboxylic acid, an aromatic sulphonic acid or an aliphatic sulphonic acid.

13. A process according to claim 1 wherein the acidic absorbent is a sulphonic acid in protonated form.

14. A process according to claim 1 wherein step (b) is carried out at a temperature of from about 20° C. to about 100° C.

15. A process according to claim 14 wherein the temperature is in the region of about 50° C. to about 95° C.

16. A process according to claim 1 wherein the reactor stream is concentrated prior to contact with the acidic absorbent.

17. A process according to claim 1 wherein the reactor stream is diluted with a solvent compatible with the absorbent before it is contacted with the absorbent.

18. A process according to claim 1 wherein the reactor stream is subjected to oxidation to break clustered catalyst prior to being contacted with the acidic absorbent.

19. A process according to claim 18 wherein the stream having been subjected to oxidation is treated to hydrocarbonylation.

\* \* \* \* \*